Figure 1:
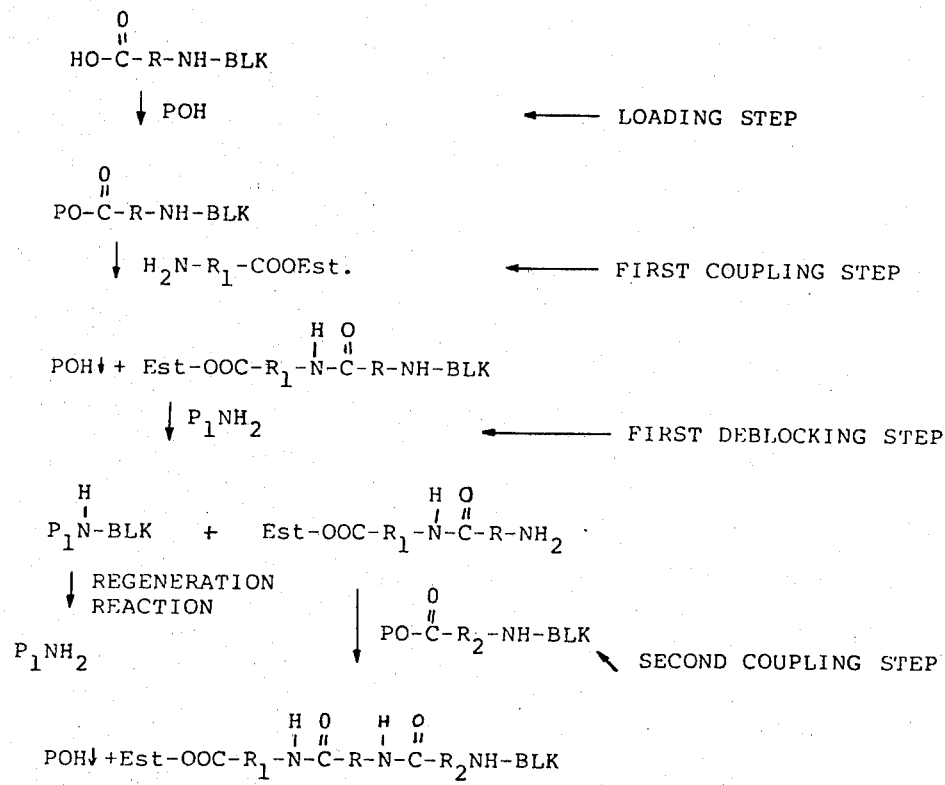

United States Patent [19]

Carpino et al.

[11] 4,394,519

[45] Jul. 19, 1983

[54] AMINO ACID BLOCKING AGENTS

[75] Inventors: Louis A. Carpino; Beri Cohen, both of Amherst, Mass.

[73] Assignee: Research Corporation, New York, N.Y.

[21] Appl. No.: 342,296

[22] Filed: Jan. 19, 1982

[51] Int. Cl.³ .......................................... C07C 125/067
[52] U.S. Cl. ....................................... 560/32; 548/533; 560/29; 560/148; 560/159; 560/160; 560/163; 260/112.5 R; 260/455 B; 260/463
[58] Field of Search ................. 560/32, 163, 160, 159, 560/29, 148; 548/533

[56] References Cited

U.S. PATENT DOCUMENTS

| | | | |
|---|---|---|---|
| 3,062,805 | 11/1962 | Albertson et al. | 560/148 |
| 3,510,504 | 5/1970 | Gerzon et al. | 560/148 |
| 3,532,736 | 10/1970 | Chamberlin | 560/148 |
| 3,775,466 | 11/1973 | Jager et al. | 560/148 |
| 3,891,692 | 6/1975 | Veber et al. | 560/163 |
| 3,906,031 | 9/1975 | Carpino et al. | 560/32 |
| 4,108,854 | 8/1978 | Gleason et al. | 560/32 |

FOREIGN PATENT DOCUMENTS 1793698  3/1973  Fed. Rep. of Germany ........ 560/32

Primary Examiner—Natalie Trousof
Assistant Examiner—Patricia M. Scott
Attorney, Agent, or Firm—Scully, Scott, Murphy, and Presser

[57] ABSTRACT

Process for the preparation of peptides including higher polypeptides utilizing indenylmethoxycarbonyl blocking groups and products produced thereby.

9 Claims, 6 Drawing Figures

BENZYL ESTER OF ALA-ALA-GLY

IIIa  R=CH$_2\emptyset$
IIIb  R=H

VIa  R=CH$_2\emptyset$
VIb  R=H
P= Polystyrene based polymer

AMINO ACID BLOCKING AGENTS

FIELD OF THE INVENTION

This invention relates generally to the field of the preparation of peptides including dipeptides, tripeptides and higher polypeptides by the sequential reaction of successive protected amino acids with each other followed by removal of the protecting groups. It relates also to novel compounds and processes utilized in the preparation of such polypeptides.

BACKGROUND OF THE INVENTION

As more and more polypeptides become of medicinal importance there is increasing incentive to improve the methods by which they may be synthesized. In recent years, peptides which have been found to be of possible pharmacological importance include those active against various cancers, diabetes, plant toxins, etc. Others have shown specific activity as growth promoters or suppressants, antibiotics, insecticides, contraceptives, antihypertensives, sleep-inducers, anti-depressants, analgesics, etc. The list is long and varied. In many cases those most interested in obtaining such materials for research, commercial or other purposes are not necessarily those with extensive experience in the art of peptide synthesis. New simplified methods of obtaining pure peptides of defined structure are clearly needed.

Currently synthesis of polypeptides in solution by classic or various repetitive methods or on a solid support (Merrifield) are popular techniques. Solution methods have the advantage of being easily monitored and allowing purification of intermediates, if necessary at any stage. A major drawback is the relative slow pace of the synthesis with each step being carried out manually.

The major advantage of the Merrifield method is its easy automation so that unattended, computer-controlled machine synthesis is possible. Unfortunately, the method suffers from an inherent deficiency due to the insoluble nature of the support on which the synthesis proceeds. Unless each acylation step occurs with 100% efficiency (an impossible goal for higher peptides), mixtures will inevitably be built up on the polymer. The longer the chain, the greater will be the contamination by undesired side reactions. Products produced in all such reactions remain to contaminate the desired product when at the end of the cycle it is removed from the polymeric matrix. The properties of these peptides will not differ sufficiently for peptides of greater than about 20-30 residues to make efficient separation feasible. The isolation of peptides of defined structure is therefore difficult for lower peptides and essentially impossible for higher peptides or proteins.

THE INVENTION

This invention combines the case of automation of the Merrifield technique with the ease of monitoring and/or purifying intermediates of the classical solution procedures, thus making it possible to carry out routine automated peptide synthesis without the danger of built-in errors during extension of the peptide chain. This object of the invention is achieved by application of a two-polymer approach utilizing polymeric reagents as opposed to polymeric supports.

In the first step of the process aspect of this invention, one polymeric ester of a protected amino acid serves to acylate an amino acid ester protected on the amino group in such a way that the product, a dipeptide ester, protected at the amino group, remains in solution. During this reaction the original phenolic polymer remains insoluble and is easily recovered by filtration.

Treatment of the protected dipeptide in solution with a second polymer acting as a deblocking agent removes the protecting group leaving the deprotected dipeptide ester in solution where it may be acylated with the same original polymer or an analogous one. After removal of the blocking group the deblocking polymer may be recovered by filtration. The polymer can be regenerated from the precipatate for reuse. The third product of the reaction is carbon dioxide which evaporates or is scavenged by excess polymer.

It is apparent then that at each step of the reaction, a desired product is produced in solution and that the byproduct is readily removed from the reaction medium since it is not soluble in the solution.

Figure 2:
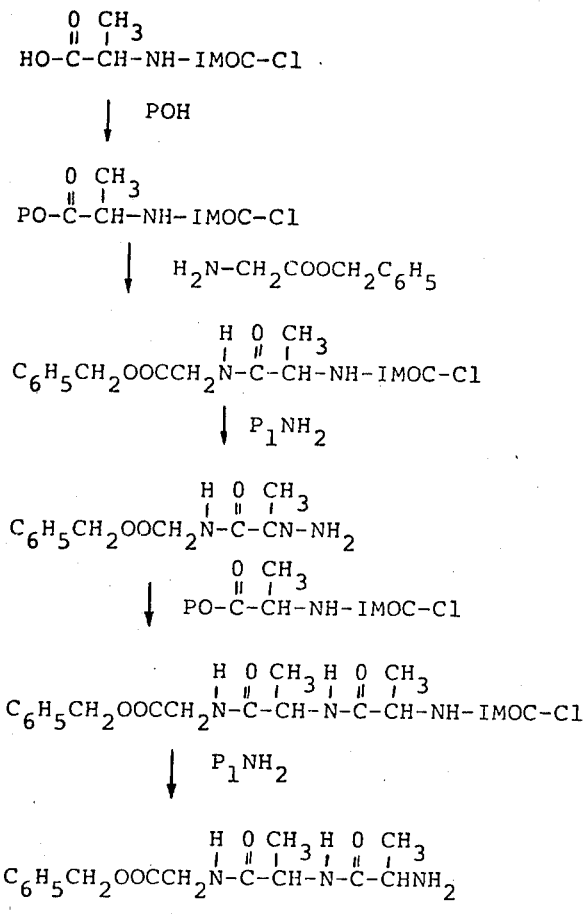

The procedure will be better understood by reference to FIGS. 1 and 2 which show respectively a generalized procedure for the production of a tripeptide and a specific procedure for the preparation of the benzyl ester alanylalanylglycine (ALA-ALA-GLY) using a specific blocking agent. In FIG. 2, the byproducts are omitted. In this specification and claims, the standard abreviations for amino acids and for certain reagents well known to peptide chemists will be adopted for convenience.

In the figures R, $R_1$ and $R_2$ represent amino acid residues, which may be the same or different; P and $P_1$ represent polymer residues; Est represents an ester group; IMOC-Cl represents the 2-chloro-1-indenylmethoxycarbonyl group (sometimes referred to herein as the Climoc group and BLK represents a blocking group selected from the group consisting of those represented by the formula:

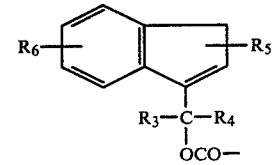

wherein $R_3$ and $R_4$ are each hydrogen, alkyl, aryl, or aralkyl containing up to nine carbon atoms; $R_5$ is up to three hydrogen atoms, or alkyl, aryl, alkaryl or aralkyl containing up to nine carbon atoms, halogen or nitro; and $R_6$ is up to four hydrogen atoms or fused phenyl, alkyl, aryl, aralkyl or alkaryl containing up to nine carbon atoms halogen or nitro. For convenience, these blocking groups are represented by the symbol BLK herein. The terms alkyl, aryl, alkaryl and aralkyl as used herein refer to groups containing only carbon and hydrogen. Those skilled in the art will recognize from a study of this specification that the groups may be substituted with reaction inert groups. There is, however, little advantage in doing so.

Novel blocked amino acids within the scope of the invention may be represented by the formula:

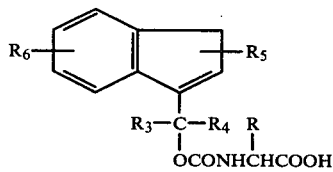

wherein R, R₃, R₄, R₅ and R₆ have the same meaning as above.

Blocked dipeptides within the scope of the invention may be represented by the formulas:

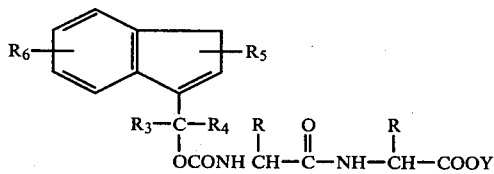

wherein R, R₃, R₄, R₅ and R₆ have the same meaning as above, and Y is hydrogen or an alkyl or aralkyl group containing up to nine carbon atoms.

Typical compounds within the scope of this invention may be represented by the formulas:

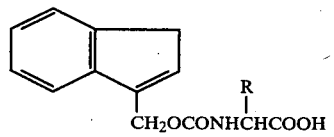
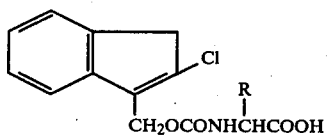
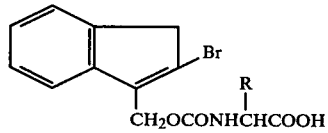
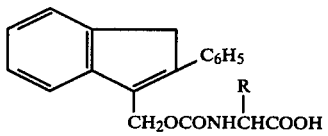
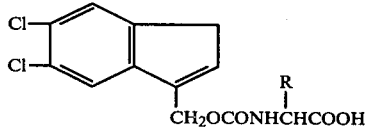
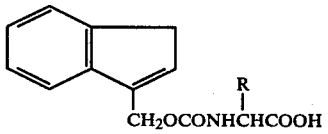
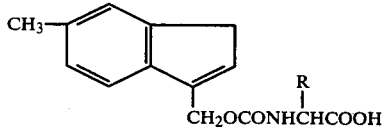
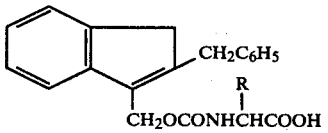

In one of its primary product aspects, this invention is concerned with novel 1-indenylmethoxycarbonyl compounds which may be substituted or unsubstituted and which are particularly characterized by the presence of a functional group attached to the carbon atom of the carbonyl function which will condense with the amino group of an amino substituted compound to form a 1-indenylmethyloxycarbonyl derivative thereof.

In its broadest aspect this phase of the invention is concerned with 1-indenylmethyloxycarbonyl compounds which may be unsubstituted or substituted with one or more reaction inert substituents. A substituent, if present, may be on the indene nucleus or the alpha carbon atom, that is the carbon atom attached to the 1-position of the indene nucleus, or it may be on the fused phenyl ring of the nucleus. The term "reaction inert" means that the substituent remains attached to the phenyl ring, the alpha carbon atom or the indene nucleus during the reaction being utilized. It may affect the reaction for example, by increasing or decreasing the rate. Typical reaction inert substituents which may be substituted on one or more positions are described above in connection with the definition of R₃, R₄, R₅ and R₆.

The unsubstituted compounds are generally suitable for most reactions involved in peptide synthesis, although substituted compounds may also be usefully employed to permit variations in the conditions under which the condensation between the amino group and the 1-indenylmethoxycarbonyl group is removed. The preferred compounds are those with a halogen or phenyl at the 2-position.

Typical compounds within the scope of this invention include compounds of the formula:

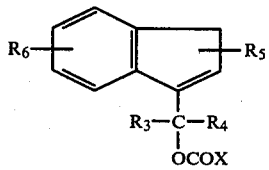

wherein R₃, R₄, R₅ and R₆ have the same meaning as above and X is: —F,—Cl,—Br,—I,—Cn,—SR₇,—SAr-,—N₃,—OAr,

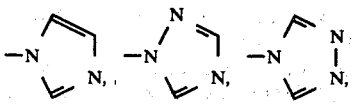

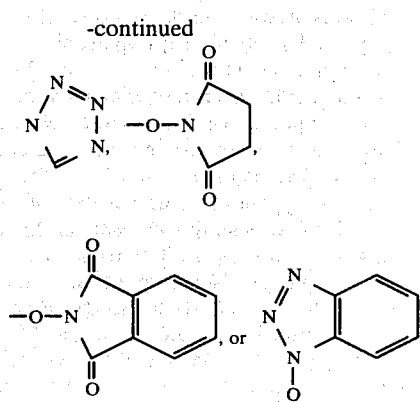

wherein $R_7$ is an alkyl group containing up to ten carbon atoms and Ar is an aryl group containing up to nine carbon atoms.

These compounds are used to prepare the novel blocked amino acids, the generic formula for which is set forth above.

PREPARATION OF NOVEL COMPOUNDS

The general procedures by which the 1-indenylmethoxycarbonyl compounds of this invention may be prepared are illustrated by the following equations wherein $R_8$ is:

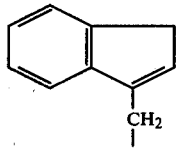

or one of the above described derivatives.

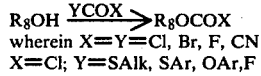
1.

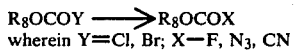
2.

Typically, reactions such are indicated by Equation (1) are carried out in a reaction inert organic solvent, suitably a halogenated hydrocarbon solvent containing up to about eight carbon atoms such as methylene chloride, ethylene dichloride or isooctane at a temperature of from about 0° C. to 25° C. during a reaction period of from about 1 to 6 hours. Suitable yields are obtained with equimolar quantities of reactants although the yield may often be appreciably increase by utilizing an excess of either one of them, for example, up to about a 20% molar excess. Generally speaking, the halogen substituted compounds are prepared under less rigorous reaction conditions than are required for the preparation of those compounds wherein the substituent is of higher molecular weight. The presence of a weak organic base, preferably a tertiary amine such as pyridine, triethylamine or quinoline may increase the rate of reaction. Up to a molar equivalent of the amine is preferably used, based on the molar amount of the halogen substituted compound employed.

Reactions of Equation (2) in which the substituent placed on the carbonyl carbon atom is initially present in an ionic form are carried out in reaction inert polar organic solvents which will enhance ionization including, for example, acetonitrile, dimethylformamide, dimethylsulfoxide, tetrahydrofuran, dioxane and others containing up to about eight carbon atoms. The reaction is normally carried out at a temperature of from about 0° C. to 25° C. during a period of from about 1 to 5 hours. Preferably equimolar quantities of reactants are employed to minimize side reactions but a moderate excess of either reactant would not introduce appreciable difficulties.

The hydroxymethyl group may be introduced at the 1-position of the selected indene starting compound by formylation followed by reduction with a mild reducing agent. For example, the initial reaction could be between indene and methyl formate in the presence of sodium ethoxide. The resulting compound could be reduced with aluminum isopropoxide or a metal hydride. The following equation is typical:

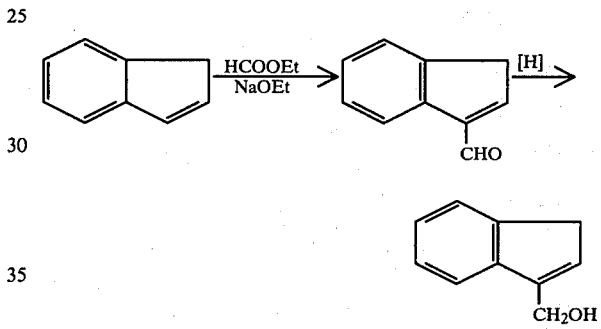

If formaldehyde is used in place of the ester and a strong base such as sodium hydride or sodamide is employed, the hydroxymethyl group can be introduced directly. Alternatively, ethyl carbonate can be used in place of ethyl formate and the ester reduced with lithium aluminum hydride.

Compounds in which the alpha carbon atom is substituted may be prepared by reaction between the selected indene compound and an aldehyde other than formaldehyde or a ketone, suitably acetaldehyde, butyraldehyde, acetone or acetophenone in the presence of sodium hydride.

Substituents in the rings can be introduced by known procedures, for example, direct bromination in the presence of metallic iron or direct nitration. Many compounds for the preparation of the blocking agents of this invention are known, or can be prepared by known procedures such as those discussed hereinabove.

PREPARATION OF BLOCKED AMINO ACIDS AND PEPTIDES

The blocking agents of this invention can be used as blocking agents for amino acids and peptides including neutral, acidic and basic amino acids. They are applicable, for example, to aliphatic amino acids including glycine, alanine, serine, valine, leucine, and isoleucine. They are applicable to aromatic amino acids including, for example, phenylalanine, tyrosine, methionine and proline. Acidic amino acids such as aspartic or glutamic and basic amino acids such as arginine and lysine can also be blocked. The compounds can also be used to block other functional groups with reactive hydrogen atoms in amino acids and peptides including hydroxyl and sulfhydryl groups.

The functional group attached to the carbonyl carbon atoms in the blocking reagents of this invention is generally one of the class which is known in the art as "leaving group". By this is meant a group which is readily broken away from its union with the carbon atoms. It is one which readily joins with an active hydrogen atom in, for example, the amino group of an amino acid or peptide, to split out a compound containing the hydrogen atom and the leaving group. Leaving groups are generally electron attracting groups either because of their electro-negativity or because they have an inductive effect. Those skilled in the art will recognize the X-substituents described above as moderate to strong leaving groups. Other such groups may also be employed in compounds within the ambit of this invention.

If the leaving group is halogen, especially chlorine, reaction may be effected in a reaction inert, polar organic solvent such as dioxane, tetrahydrofuran, dimethylformamide, pyridine or other solvent containing, for example, up to eight carbon atoms under alkaline conditions, typically adilute aqueous alkali metal base such as sodium or potassium hydroxide or carbonate, at low temperature, for example, from about 0° C. to 25° C. during a period of from about 2 to 3 hours. Usually the protected amino acid or peptide will precipitate upon acidification of the mixture, and may be purified by any appropriate method such as recrystallization. Excess blocking reagent may be employed, even up to 0.5 molar excess, but equimolar quantities of reactants generally give better results.

If the alpha carbon atom is substituted as described above, it is best to avoid strong leaving groups such as chlorine, bromine or iodine since the resulting tertiary systems, including the α-carbon atom, tend to be unstable and may decompose, as will be recognized by those skilled in the art.

The following Table 1 shows typical reaction conditions for a variety of X-substituents within the scope or this invention. They are generally listed in increasing order of the ease with which they are replaced. Chlorine, which is the strongest leaving group listed and the easiest to replace is listed first.

conditions involved in the removal of most of the commonly used protective groups such as hydrogen bromide or chlorine in various organic solvents, and trifluoroacetic acid. This is a special advantage of these particular compounds of this invention which coupled with alkaline cleavage greatly increases the options available to the skilled peptide chemist for the preparation of complex polypeptides. The presence of various substituents will affect stability in accordance with principles well known to those skilled in the art.

For coupling an N-protected amino acid or peptide of this invention with a free amino group of another amino acid or peptide to produce di-, tri-, and higher oligopeptides, any of a wide variety of procedures are available. Generally speaking, most of the coupling procedures normally employed by the skilled practitioner can be used. Since these procedures are quite standardized, they will not be discussed in detail.

The azide method can be employed. The use of activated esters, suitably aryloxy or thioaryl esters, especially substituted phenyl esters such as p-nitrophenyl esters leads to satisfactory results. In fact, most of the procedures used for the placement of the 1-indenylmethoxycarbonyl function for the protection of an amino group can be used for the coupling reaction.

One coupling procedure which is especially favored is to convert the protected amino acid or peptide to an N-hydroxy succimimide ester. This may be accomplished using dicyclohexylcarbodiimide. The ester is coupled with the amino group under alkaline conditions in a reaction inert, polar, organic solvent such as an ester, ether or alcohol containing up to about six carbon atoms. Any mild alkaline reagent such as alkali metal hydroxides, carbonates or bicarbonates, or alkali metal salts of lower aliphatic carboxylic acids can be employed. If the amino acid or peptide to be coupled is in the form of an ester, sodium acetate in water is the preferred alkaline reagent. If it is in the form of a free acid sodium hydroxide is the preferred reagent. The reaction takes place at from about 15° C. to 30° C. during a period of from about 10 to 50 hours. It is generally most economical to use a slight molar excess, say up to about 20% molar excess of one of the reactants, although equimolar quantities can also be employed.

CLEAVAGE OF THE PROTECTING GROUP

TABLE 1

| | Temperature | Time | Carrier | Mole Ratio reagent:amino | Conditions |
|---|---|---|---|---|---|
| Cl | 0°–25° C. | 2–3 hrs. | organic solvent | 1:1 to 1.5:1 | alkaline |
| Br | " | " | " | " | " |
| I | " | " | " | " | " |
| $N_3$ | " | 3–5 hrs. | " | " | neutral or alkaline |
| 2,4-$(NO_2)_2$—$C_6H_3$ | " | " | " | " | " |
| $C_6Cl_5$ | " | " | " | " | " |
| CN | " | " | " | " | " |
| SAlk | 25°–50° C. | 8–12 hrs. | " | " | " |
| P—$NO_2C_6H_1$ | " | " | " | " | " |
| P—Cl—$C_6H_3$ | " | " | " | " | " |
| 3,4-$(Cl)_2$—$C_6H_3$ | " | " | " | " | " |
| 2,4,6-$(Cl)_3$—$C_6H_2$ | " | " | " | " | " |
| 2,4,5$(Cl)_3C_6H_2$ | " | " | " | " | " |

PREPARATION OF PEPTIDES

The 1-indeylmethoxycarbonyl group, once placed on the amino function to be protected is especially stable. This makes it possible to use a variety of methods for forming peptides without danger of cleavage of the protecting group. In fact, the group is stable under As mentioned above, a special advantage of the particular novel compounds of this invention as blocking agents for amino acid and peptides is that they can be cleaved under mildly alkaline conditions. Another feature is that the conditions of cleavage can be varied by varying substituents on the indenyl group, especially the alpha carbon atom. This makes it possible to remove the protecting group under a variety of conditions specially selected to avoid affecting other groups which may be present in the molecule. It is even possible to cleave the protecting group under acid as well as alkaline conditions especially if the alpha carbon atom is substituted with at least one aryl group or with two alkyl groups.

Any of a variety of non-hydrolytic alkaine reagents may be employed for removal of the protecting group.

Primary, secondary and tertiary amines having a pk$_a$ value of at least about 6 may be usefully employed. Typical examples of useful amines include triethyl amine, ethanolamine, morpholine, piperidine, diethyl amine and ethyl amine. The monomer may be removed by extration with an organic solvent, for example, ether. The polymer is insoluble in water and normally separated by filtration after converting the amine acid or peptide from which the protecting group has been removed to a water soluble form. With alkaline reagents which are liquid at room temperature, the reaction temperature is normally from about 0° C. to 30° C. Best results are obtained utilizing an excess of the alkaline reagent. The time of the reaction will vary appreciably with the selected reagent and the degree of the excess alkaline reagent employed.

Figure 3:
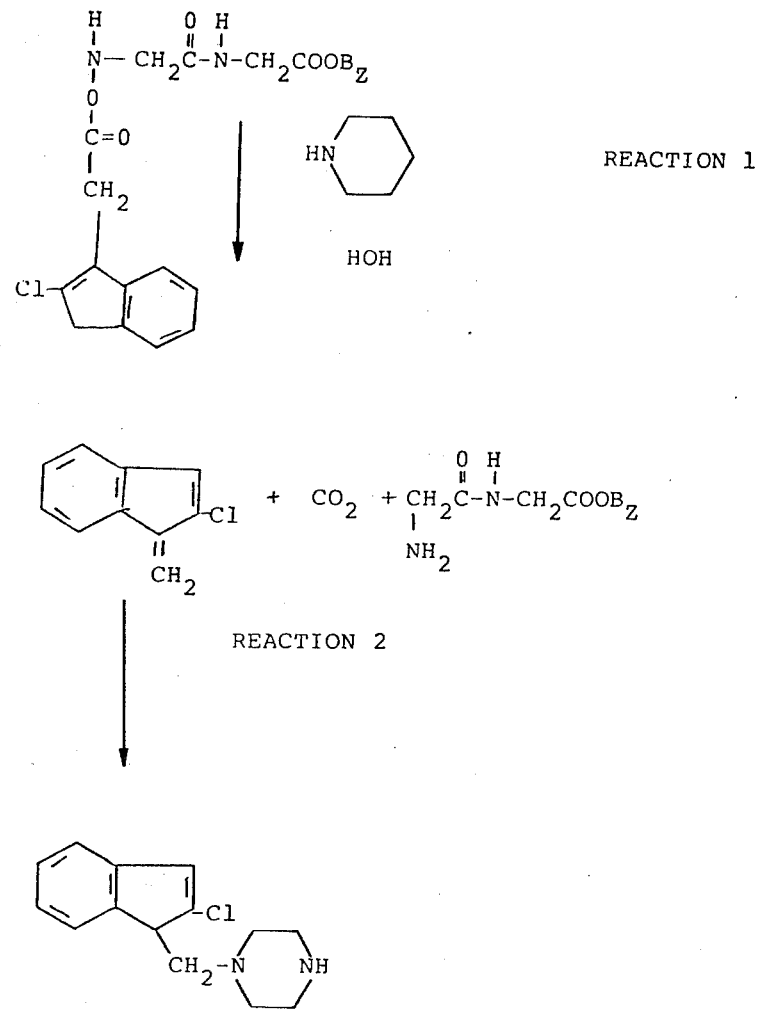

FIG. 3 shows in more detail the specific reaction which takes place when the 1-indenylmethoxycarbonyl group is removed from a dipeptide using a cyclic secondary amine such as piperidine. The dipeptide is the benzyl ester of GLY-GLY.

It has been observed that the cleavage of the blocked dipeptide (Reaction 1) to form 2-chloro benzofulvene, carbon dioxide and the deblocked dipeptide ester followed by reaction of the benzofulvene with the piperazine, or other secondary amine (Reaction 2), takes place rapidly, i.e. less than five minutes. With primary, secondary and tertiary amines, Reaction 1 takes place rapidly, but it is only with cyclic secondary amines that Reaction 2, i.e. adduct formation, takes place rapidly. Adducts form relatively slowly with primary amines and with tertiary amine, they do not form at all. With most secondary amines, the overall reaction of FIG. 3 is essentially instantaneous.

U.S. Pat. Nos. 3,835,175 and 3,906,031 describe the use of the chloroformate of 9-fluorenyl methanol and related compounds as blocking agents for amino acids in the preparation of peptides. The chloroformate is an excellent reagent and has proved to be useful in the preparation of a large number of peptides. The removal of the 9-fluoromethoxycarbonyl group from a peptide moiety to form the free peptide is, as with the compounds of this invention, effected with weak bases such as amines. The removal, however, is much slower than with the compounds of this invention. Moreover, the rate at which the dibenzofulvene is scavenged from the reaction mixture in the form of adducts by reaction with primary or secondary amine catalysts is unexpectedly slow compared with the rate at which benzofulvene is removed from a reaction mixture. Benzofulvene is the byproduct which forms when the indenylmethoxycarbonyl (IMOC) protecting group is removed from a protected amino acid in accordance with this invention.

With most secondary amines the formation of adducts with dibenzofulvenes requires at least ten minutes and, depending on the selected compounds and reaction conditions may require several hours. The comparable reaction with monobenzofulvenes, as indicated above, is essentially instantaneous. Comparable rates apply for the formation of adducts with primary amines. With tertiary amines, no adduct formation takes place. As will be discussed in more detail hereinafter, whem polymers are utilized for deblocking and adduct formation the overall reaction when dibenzofulvene is the byproduct may require as long as twenty-four hours. With benezofulvene, it is a matter of minutes.

THE TWO-POLYMER SYSTEM

The two-polymer system of this invention will now be discussed in more detail.

As shown in FIG. 1, the first step of the sequence is a loading step in which a blocked amino acid prepared as described hereinabove, is converted to a polymeric ester by reaction with an hydroxylated polymer. Any of a number of polymers are known or can be prepared are suitable for this reaction. These include, for example, cross linked polystyrenes which may be represented by the partial formulas:

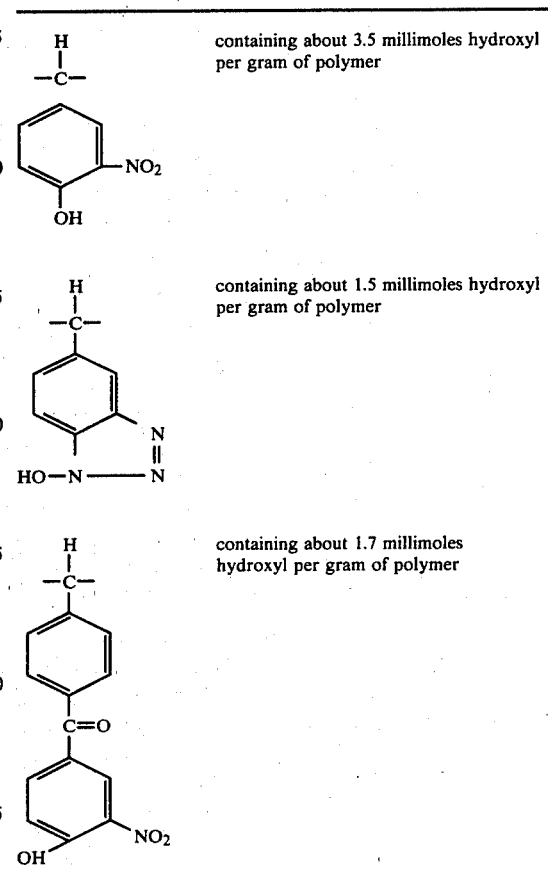

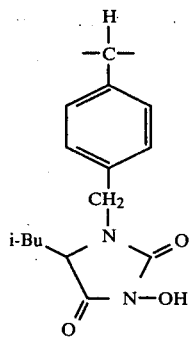

containing about 0.9 millimoles hydroxyl per gram of polymer

These and other equivalent polymers, their methods of preparation, and procedures for varying the hydroxyl content are known.

The preparation of the polymeric ester by dehydration between the acid group of an amino acid or peptide and the polymeric alcohol may take place using any of the usual procedures for forming esters. A preferred procedure is to use a dehydrating agent which is inert toward the amino acid or peptide, i.e. one which will not cause racemization, even partial racemization of the blocked amino acid or peptide. The selected dehydrating agent, therefore, will be one which effects dehydration under mild conditions. A number of such reagents are available. One such class is the carboiimides such as decyclohexyl carbodiimide and benzyl butyl carbodiimide. The reaction takes place in a reaction inert, polar, organic solvent which is preferably, anhydrous, at a temperature of from −10° C. to 25° C. during a period of from one to five hours. Suitable solvents include esters and ethers containing up to about eight carbon atoms such as ethyl acetate, butyl acetate, tetrahydrofuran, diethyl ether, dioxane, chloroform, methylene dichloride and dibutyl ether. While the desired product will form even with an excess of the acid, it will be recognized that it is best to employ a molar excess, even up to a 2- or 3-molar excess of reagents so as to insure as complete reaction as possible of the amino acid or peptide. The product is an amino blocked polymeric ester of an amino acid or peptide.

As this description proceeds, those skilled in the art will recognize that the overall procedure is applicable to the buildup of peptides by the addition of one amino acid at a time, or by the addition of one peptide to another peptide, for example, a tirpeptide to a tetrapeptide. For convenience, hereinafter reference will normally be made to amino acids, but it will be recognized that the term could include peptides. For example, it will be recognized that where a polymeric ester of an amino acid is employed, a polymer ester of a peptide could be equally useful.

It will be apparent, also, that in the course of the synthesis, it may be necessary to protect certain groups to prevent unwanted side reactions. For example, it may be necessary to protect the hydroxyl group of tyrosine, a delta or gamma carboxyl group of aspartic or glutamic acid, ot the epsilon amino group of lysine so as to prevent interference by these groups in the main desired reaction. This is a common problem in peptide synthesis and many procedures are available for dealing with it. Such procedures are known to the skilled peptide chemist.

In the next step of the synthesis, an amino acid with a free amino group and a protected carboxyl group is reacted with the thus prepared amino blocked amino acid polymeric ester as shown in FIG. 1.

Any of the usual groups employed for protecting or blocking carboxyl groups in peptide chemistry can be employed in this instance. The principal criteria for selection of such groups, as is well known is that they be easily placed on, stable, and easily removed. Generally, the most preferred procedure is to form esters, and this is the preferred procedure for this reaction. The preferred esters are alkyl or alkaryl groups containing up to eight carbon atoms such a methyl, ethyl, tert-butyl, phenyl, benzyl, or p-methylbenzyl.

Coupling reaction with regeneration of the polymer takes place in a reaction inert organic solvent, suitably a hydrocarbon or halogenated hydrocarbon solvent containing, for example, up to eight carbon atoms such as methylene chloride, chloroform, ethylene dichloride, heptane, tetrahydrofuran, dioxane, or isooctane. The reaction is generally carried out at ambient temperature, i.e. 20° C. to 40° C. during a period of about one-half to three hours. The polymer does not dissolve, but as the blocked amino acid on the polymer reacts with amino ester the resulting peptide is cleaved from the polymer and dissolves.

While, theoretically, the amino acid ester will react with an equimolar quantity of the blocked amino acid on the polymer, it is preferred to use a sufficient amount of loaded polymer to provide an excess of blocked amino acid. This insures as complete a reaction as possible. The polymer carrying the unreacted, blocked amino acid can be separated from the reaction, washed with solvent, reloaded and used in subsequent coupling reaction.

The products of this coupling reaction are the polymer and the peptide. In the peptide, the amino end is blocked with IMOC group or a selected derivative and the carboxyl end is blocked with an ester group. The next step in the synthesis is the removal of the amino end blocking group.

Deblocking is accomplished by reaction of the blocked peptide with a polymer carrying an amine function, preferably a secondary amine. A number of polymers are available or can be prepared by procedures known to those skilled in the art. These include, for example, cross linked polystyrenes and silica dioxide polymers represented by the formulas:

| Structure | Description |
|---|---|
| 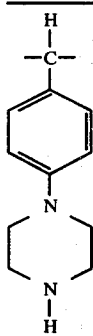 | cross linked with 1 to 4% divinyl benzene and containing about two milliequivalents NH per gram of polymer |
| 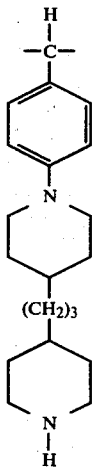 | cross linked with 1 to 4% divinyl benzene and containing about two milliequivalents NH per gram of polymer |
| 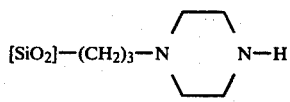 | containing about 1.2 milliequivalents per gram of polymer |
| 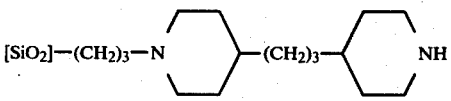 | containing about 0.5 milliequilvalents per gram of polymer |
| 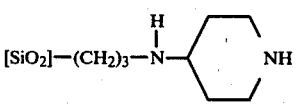 | containing about 1 milliequivalent per gram of polymer |

These and other equivalent polymers, their method of preparation, and procedures for varying their NH content are known.

The reaction conditions for removal of the blocking group with the polymer are similar to those for the coupling reaction. It is effected in the same types of hydrocarbon, ether or halogenated hydrocarbon solvents in the same temperature range. However, the reaction period may be somewhat longer, for example, 15 minutes to two hours.

As will be apparent, particularly from a consideration of FIGS. 1 and 3, two swquential reactions take place in the deblocking reaction medium. The first is the removal of the deblocking group as monobenzofulvene or a derivative thereof with simultaneous generation of the free peptide ester and of carbon dioxide. The free peptide stays in solution and the carbon dioxide exits in the reaction mixture.

The second reaction is the formulation of an adduct by reaction of the benzofulvene with the amine on the polymer.

It is the second reaction which brings out a most important and unexpected aspect of this invention, that is, the unexpectedly high rate at which the adduct forms. This rate is so fast that the overall reaction takes place, as indicated above, in 15 minutes to 2 hours. A very significant that results from this high rate of reaction is that the complete synthesis can be automated.

In the Journal of The Chemical Society, Chemical Communications, 450(1978), an analogous reaction is described in which a piperazine polymer formed from chloromethylated polystyrene was employed to deblock amino acids, the amino group of which had been protected with the 9-fluorenylmethoxycarbonyl group. The byproduct formed was therefore dibenzofulvene in contrast to the monobenzofulvene of this invention. An adduct, analogous to the adduct of this invention forms by a reaction of the dibenzofulvene with the piperazine on the polymer. In methylene chloride, the reaction required twelve to twenty-four hours for completion. It could be accelerated by the addition of methanol or formamide, but the reaction still required six to eight hours for completion. In fact, the reaction appears never to be 100% complete. A small equilibrium concentration seems always to be present. The time required for the reaction renders it wholly unsuitable for automation which, to be practiced for the preparation of peptides, particularly higher peptides, requires quick, repetitive cycles in which the reaction times at each step of the cycle are as fast as possible and preferably under three hours.

At the end of the deblocking step in the reaction sequence of this invention, the polymer can be collected by filtration, washed and regenerated. A useful regeneration procedure is to take up the adduct in a basic ragent such as potassium hydroxide-dioxane-water or piperidine. The mixture is allowed to stand at ambient temperature for about ten to twelve hours, and the regenerated polymer recovered by filtration.

The product which results from the deblocking step is a dipeptide with a free amino group and an esterified carboxyl terminus. As can be seen from the figures, this peptide is suitable for coupling through its free amino group with a polymer ester of another blocked amino acid.

As can be readily understood from the foregoing description of this invention, one of its truly significant advantages is that the blocked amino acid, blocked peptide or unblocked peptide are soluble in the reaction medium whereas the polymers, both esterifying and deblocking, as well as the loaded hydroxyl polymer and amine polymer, are insoluble. These solubility relationships permit easy separation of the desired product from the byproduct at each stage of the synthesis.

It sometimes happens that the solubility relationships are not as straightforward as this, however. For example, if the amino acid members of a peptide may be insoluble or only soluble in hydrocarbon or halogenated hydrocarbon medium. Also, as the number of amino acids in the peptide increases, the total molecular weight increases and the solubility of the peptide decreases.

The problem can often be solved by the addition of a reaction inert, polar, organic solvent which is miscible with the hydrocarbon or halogenated hydrocarbon solvent. These solubility enhancers include, for example, ethers, esters, carbamides and sulfoxides, amyl acetate, dimethylformamide, dimethyl sulfoxide and the like.

Solubility can also be enhanced by incorporating removable solubilizing groups in the peptide as its molecular weight increases. This can be accomplished by using for the coupling step, amino acids whose amino group has been partially blocked by replacing one of the hydrogens with a solubilizing group which will improve solubility in the selected solvent or solvent mixture. The selected group should, of course, be one which is readily removed. Groups which may be employed include methoxymethyl, cyclopropylmethyl, benzyl and trimethylsilyl.

Since the solubilizing group is on the free amino group of the amino acid ester used in the coupling reaction, it will ultimately replace the hydrogen of the peptide bond. Such novel compounds would, therefore, be represented by the formula:

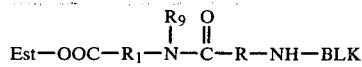

wherein Est, BLK, R and $R_1$ have the same meaning as above and $R_9$ is selected from the group consisting of methoxymethyl, cyclopropylmethyl, dicyclopropylmethyl, benzyl and trimethylsilyl.

The following non-;imiting examples are given by way of illustration only.

EXAMPLE 1

2-CHLORO-1-INDENYLMETHANOL (I)

A flask is charged with 75 gr (0.5 mol) 2-chloroindene, 50 ml (0.6 mol) ethyl formate, 400 ml dry ether and 23 gr (0.6 mol) sodium hydride (50–60% dispersion in oil). The mixture is heated to reflux to start the reaction, as indicated by a vigorous hydrogen evolution. The flask is cooled in an ice water bath, until hydrogen evolution subsides, then refluxed again for an additional ten minutes. Excess sodium hydride is carefully decomposed with water, and more water is added to form two layers. The aldehyde dissolves in the aqueous basic solution which is extracted several times with ether. To the aqueous solution are added 19 gr (0.5 mol) sodium borohydride. With vigorous stirring and cooling in an ice water bath, glacial acetic acid is added dropwise at a rate of a drop per second, until the mixture becomes acidic. The alcohol is extracted with ether and the organic solution dried and evaporated. The crude alcohol (75 gr, 83%) is recrystallized from carbon tetrachloride, to give white crystals, m.p. 104°–105° C. Elemental analysis: Calc. for $C_{10}H_5ClO$: C, 66.49%. H, 5.02%. Cl, 19.63% Found: C, 66.20%. H, 5.02%. Cl, 19.90. NMR spectrum ($CDCl_3$, $\zeta$ppm): 2.05 (s, 1H), 3.50 (s, 2H), 4.65 (t, 2H), 7.1–7.6 (m, 4H).

A similar procedure is utilized to prepare:
1-Indenylmethanol
1-Benz(f) indenylmethanol
2-Bromo-1-indenylmethanol
2-Phenyl-1-indenylmethanol
5-Methyl-1-indenylmethanol
2-Benzyl-1-indenylmethanol
2-(4-Methylbenzyl)-1-indenylmethanol

EXAMPLE 2

2-CHLORO-1-INDENYLMETHYLCHLOROFORMATE (II)

18 gr (0.1 mol) of the alcohol I are dissolved in 100 ml dry THF, the the mixture cooled to 0° C., 30 gr (0.3 mol) of phosgene added, and the mixture stirred at 0° C. for three hours. Excess phosgene and the solvent are removed at water pump vacuum at 0° C. The residue is recrystallized from hexane. m.p. 62°–63° C. 22 gr. A 91% yield of the chloroformate is obtained. Elemental analysis: Calc. for $C_{11}H_8Cl_2O_2$: C, 54.35%. H, 3.32%. Cl, 29.17%. Found: C, 54.63%. H, 3.17%. Cl, 28.95%. NMR ($CDCl_3$): 3.5 (s,2H), 5.25 (s,2H), 7.15–7.4 (m,4H).

A similar procedure is utilized to prepare the chloroformates of the compounds prepared in Examples 1 and 2, namesly:
1-Indenylmethylchloroformate
1-Benz (f) indenylmethylchloroformate
2-Bromo-1-indenylmethylchloroformate
2-Phenyl-1-indenylmethylchloroformate
5-Methyl-1-indenylmethylvhloroformate 2-Benzyl-1-indenylmethylchloroformate
2-(4-Methylbenzyl)-1-indenylmethylchloroformate

EXAMPLE 3

PREPARATION OF Cl-IMOC PROTECTED PHENYLALANINE (IIIa)

8.25 Gr (50 mol) phenylalanine are dissolved in 150 ml 06.N sodium carbonate and cooled at 10° C. A chilled solution of 13 gr (54 mol) of the chloroformate II in 150 ml of dioxane is added and the mixture stirred with cooling in an ice water bath for five hours. The solid which forms contains the sodium salt of the protected amino acid. It is filtered and washed several times with ether, then suspended in water and concentrated hydrochloric acid is added to liberate the Climoc-phenylalanine. The aqueous solution is extracted several times with ether, filtered and acidified with concentrated hydrochloric acid. The resulting solid is combined with that obtained as described above. Yield-17 gr (92%) These are washed with water and crystallized from water-methanol. m.p. 146C. Elemental analysis: Calc. for $C_{20}H_{18}ClNO_4$: C, 64.61%. H, 4.88%; N, 3.77%. Cl, 9.53%. Found: C, 63.20%. H, 4.96%. N, 3.70%. Cl, 9.22%. NMR (CDCl$_3$): 3.6 (s, 2H), 3.95–4.2 (d, 2H), 5.2 (s, 2H), 5.6–5.9 (t, 1H), 7.2–7.6 (m, 4H).

A similar procedure is utilized to prepare:
N-(2-chloro-1-indenylmethoxycarbonyl)glycine (IIIb)
N-(1-indenylmethoxycarbonyl)alanine
N-(1-benz(f) indenylmethoxycarbonyl)alanine
N-(2-bromo-indenylmethoxycarbonyl)leucine
N-(2-phenyl-1-indenylmethoxycarbonyl)valine

EXAMPLE 4

PREPARATION OF Cl-IMOC PROTECTED GLYCYL CHLORIDE (V)

Climoc-glycine (IIIb, 2.8 g, 10 mol) is suspended in chloroform (10 mL) and 3 mL thionyl chloride added. The mixture is refluxed for 10 min, during which the solid acid is dissolved. The reaction mixture is cooled, filtered and 100 ml hexane added to precipitate the acid chloride. Filtration afforded 2.3 g (77% yield). M.p. 75 C (dec.). Anal. Calc. for $C_{13}H_{11}O_3NCl_2$: C, 52.02%; H, 3.69%; N, 4.67%; Cl, 23.62%. Found: C, 52.27%; H, 3.62%; N, 4.72%; Cl, 21.94%. NMR: 3.5 (s, 2H), 4.25 (d, 2H, j=12 Hz), 5.15 (2, 2H), 5.5–5.85 (m, 1H), 7.15–7.5 (m, 4H).

EXAMPLE 5

PREPARATION OF POLYMERIC ESTER DERIVATIVE OF Cl-IMOC PROTECTED PHENYLALANINE (VIA)

740 mg (2 mmol) of Climoc-phenylalanine IIIa are dissolved in 7 ml of THF and 1 gr of a polymer containing 4-hydroxy-3-nitrobenzophenone groups, 1.7 mmol/gr added. The mixture is cooled to −10° C. and 400 mg (2 mmol) of benzyl butyl carbodiimide added. After stirring at a temperature not exceeding −5° C. of three hours, the polymer is washed with chilled dry THF (4×15 ml), then with methylene chloride (3×15 ml) and finally with ether. It is then dried by passing a slow stream of air through it. The final polymer contains 0.55 mmol/gr of phenylalanine residues attached to it as calculated by its chlorine analysis (1.95% chlorine). Similarly, the polymeric active ester of Climoc-glycine Vb is prepared. The resulting polymer contains 0.52 mmol/gr glycine residues.

EXAMPLE 6

Cl-IMOC PHE-LEU BENZYL ESTER (VII)

600 mg (1.5 mmol) leucine benzyl ester p-toulene sulfonate is neutralized with excess sodium bicarbonate solution and extracted into 35 ml methylene chloride. This solution is added to 6 gr of the polymer VIa. After stirring for half an hour, the polymer is washed with 8×15 ml portions of methylene chloride. The combined washings are evaporated to afford 820 mg (95%) of the Climoc-Phe-Leu-OBzl dipeptide (VII), m.p. 131°–132°. Elemental analysis: Calc. for $C_{33}H_{35}ClN_2O_5$: C, 68,92%. H, 6.13%. N, 4.8%. Found: C, 67.65%. H, 6.09%. N, 4.76%. NMR spectrum (CDCl$_3$, ζppm) 0.75-0.95 (d, 6H), 1.4-1.7 (m, 3H), 2.95-3.2 (d, 2H), 3.55 (s, 2H), 4.4-4.75 (m, 2H), 5.15 (s, 4H), 5.35-5.55 (d, 1H), 6.3-6.6 (d, 1H), 7.15-7.6 (m, 14H).

The following compounds are similarly prepared:
Cl-IMOC-PHE-ALA-BenzylEster
Cl-IMOC-LEU-GLY-BenzylEster
Cl-IMOC-ILEU-VAL-BenzylEster

EXAMPLE 7

Cl-IMOC-GLY-PHE-LEU BENZYL ESTER VIII

The Cl-IMOC-Phe-Leu benzyl ester (VII) from the previous example is deblocked by a polymer containing piperazine moieties (2 mmol/gr) by dissolving the peptide in chloroform and adding 8 gr of the polymer. The mixture is stirred for one and one-half hours. The polymer is washed with 6×100 ml portions of methylene chloride and the combined washings evaporated to yield 495 mg (90%) of the free amino peptide. This, in turn is dissolved in 30 ml methylene chloride and reacted with 5 gr of the polymer Vb for one hour. The polymer is washed as described for the dipeptide, to afford 740 mg (91%) of the tripeptide Climoc-Gly-Phe-Leu-OBzl, m.p. 105 C. (dec.). Elemental analysis: Calc. for $C_{35}H_{39}Cl_1N_3O_6$: C, 66.35%. H, 6.32%. Cl, 5.52%. N, 6.63%. Found: C, 66.79%. H, 6.32%. Cl, 5.41%. N, 7.07%. NMR spectrum: 0.75-0.95 (d, 6H), 1.35-1.75 (m,3H), 1.9-2.05 (d, 2H), 3.50 (s, 2H), 3.7-3.9 (d, 2H), 4.5-4.85 (m, 2H), 5.1 (s, 4H), 5.6-5.9 (t, 1H), 6.7-7.5 (m, 16H).

EXAMPLE 8

FMOC-TYR(OBZL)-GLY-GLY-PHE-LEU-OBZL (X)

400 mg (1.0 mmol) leucine benzyl ester p-toulene sulfonate is neutralized with excess sodium bicarbonate solution and extracted into 20 ml methylene chloride. This solution is added to 4 g of polymer VIa. After stirring for 30 min, the polymer is washed with 8×15-ml portions of methylene chloride. The combined washings are evaporated to a volume of 10 ml and reacted with 7 g of a modified silica containing 0.92 mmol/g of 4-aminomethylpiperidine groups for 20 min. The silica is washed with 8×10 ml of methylene chloride and the combined washings evaporated to a volume of 10 ml and reacted with 5 g of the polymer VIb for 40 min. The polymer is washed with 8×10 ml of methylene chloride. The combined washings are evaporated to a volume of 10 ml and reacted with 7 g of the modified silica for 30 min. Washing as described above and reacting the deblocked peptide with 5 g of VIb results in the tetrapeptide Climoc-Gly-Gly-Phe-Leu-Obzl IX. It is washed from the polymer as described above, deblocked by the modified silica and reacted with the polymeric active ester of the benzyl ester of fluornylmethoxycarbonyltyrosine, [Fmoc-tyrosine(Obzl)], for 2 hours to give, after chromatography, 595 mg (63% yield) of the pentapeptide Fmoc-Tyr(Obzl)-Gly-Gly-Phe-Leu-Obzl) X, m.p. 172 C. (dec). It has an identical NMR spectrum with the same pentapeptide prepared by conventional solution techniques. Further evidence for its structure is obtained by deblocking of all protecting groups, by catalytic transfer hydrogentation, of a 5 mg sample of the peptide, with 0.5 ml solution of 3% ammonium formate in methanol-dioxane (1:1), adding 10 mg of 10% Pd-C catalyst, for 1 hour TLC separation of the reaction mixture (chloroform-methanol-acetic acid-water 30:20:6:4) and spraying with ninhydrin reveals only two spots, one corresponding to ammonium formate, the other having an identical Rf (0.50) with a commercial sample of the free peptide (Chemical Dynamics Corp.). In a separate experiment, the synthesis described above is stopped at the tetrapeptide stage. Climoc-Gly-Gly-Phe-Leu-Obzl IX is obtained in a 74% yield after chromatography. M.p. 233 C. Anal: Calc. for $C_{37}H_{41}O_7N_4Cl$: C, 64.48%; H, 6.00%; N, 8.13%; Cl, 5.14%. Found C, 64.51%; H, 6.16%; N, 7.95%; Cl, 5.09%. H NMR (CDCl$_3$) 0.7-0.9 (m, 6H), 1.45-1.75 (m, 3H), 2.85-3.15 (m, 2H), 3.45 (s, 2H), 3.8-4.2 (m, 5H), 6.5-6.8 (m, 1H), 5.05 (s, 2H), 5.15 (s, 2H), 4.2-4.4 (m, 1H), 7.1-7.4 (m, 14H), 7.6-7.9 (m, 2H).

Figure 4:
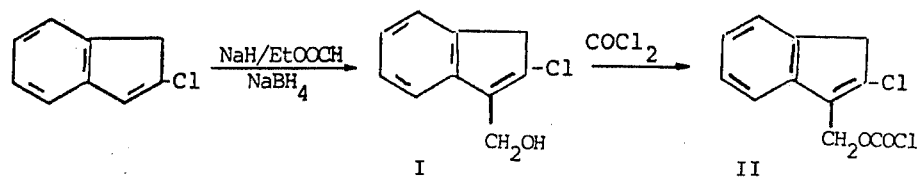
Figure 4:
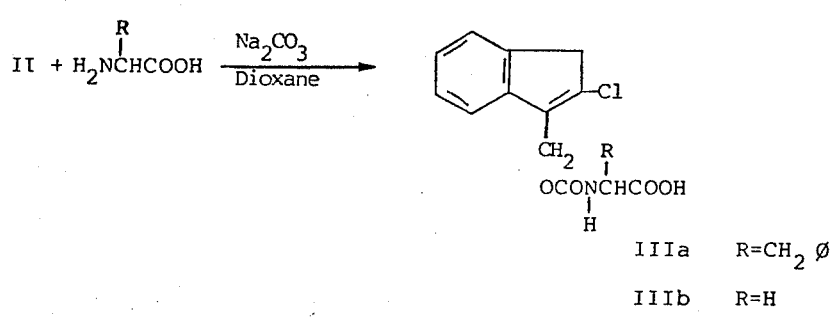
Figure 4:
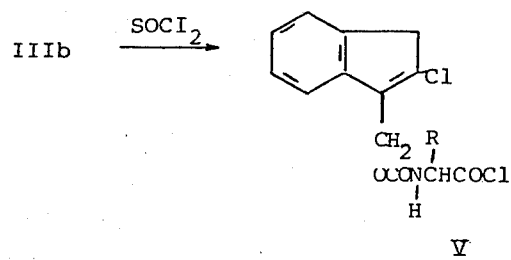
Figure 4:
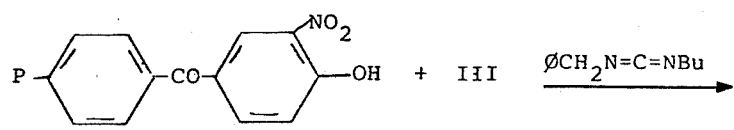
Figure 4:
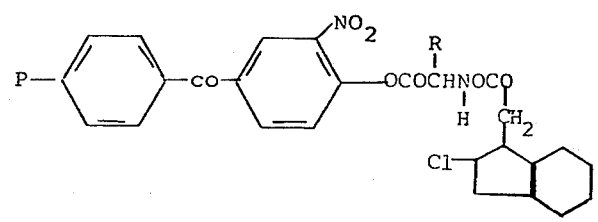
Figure 5:
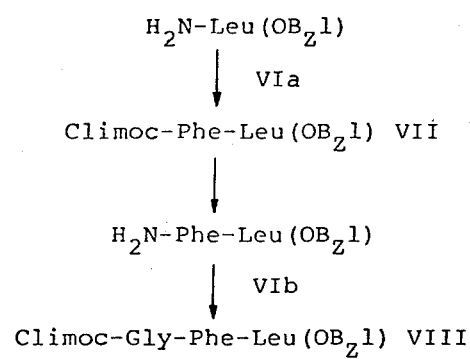
Figure 6:
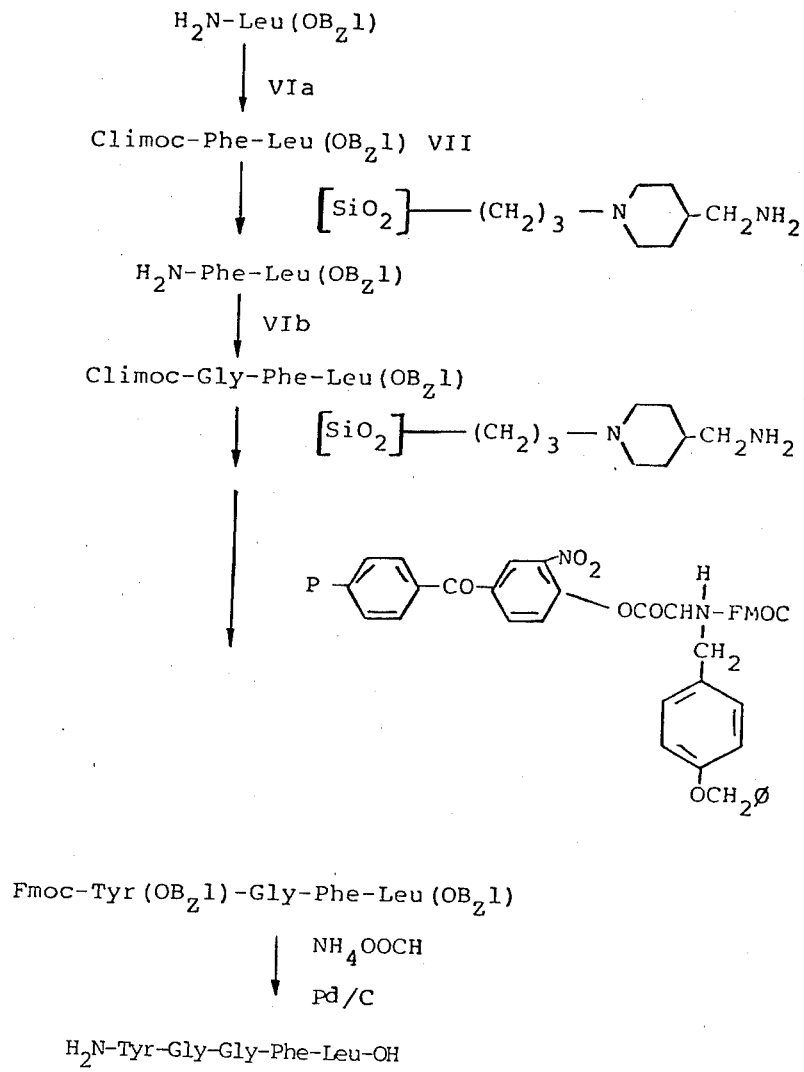

The principal examples are summarized in FIGS. 4, 5 and 6.

What is claimed is:

1. A protected amino acid of the formula:

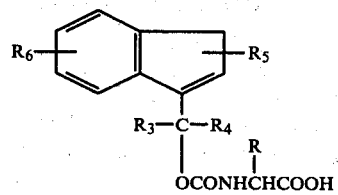

wherein R is an amino acid residue; $R_3$ and $R_4$ are each hydrogen, alkyl, aryl or aralkyl; $R_5$ is up to three hydrogen atoms, alkyl, aryl, alkaryl aralkyl, halogen or nitro; and $R_6$ is up to four hydrogen atoms, fused phenyl, alkyl, aryl, alkaryl, aralkyl, halogen or nitro; the alkyl, aryl, alkaryl or aralkyl group containing up to nine carbon atoms.

2. A protected amino acid of claim 1 wherein $R_3$, $R_4$ and $R_6$ are hydrogen and $R_5$ is a 2-halogen.

3. A protected amino acid of claim 2 wherein $R_5$ is 2-chloro.

4. A protected amino acid of claim 1 wherein $R_3$, $R_4$ and $R_6$ are hydrogen and $R_5$ is 2-phenyl.

5. N-(2-chloro-1-indenylmethoxycarbonyl)phenylalanine.

6. N-(2-chloro-1-indenylmethoxycarbonyl)glycine.

7. N-(1-indenylmethoxycarbonyl)glycine.

8. N-(1-benz(f) indenylmethoxycarbonyl)glycine.

9. N-(2-phenyl-1-indenylmethoxycarbonyl)glycine.

* * * * *